(12) United States Patent
Fathollahi et al.

(10) Patent No.: US 9,097,723 B2
(45) Date of Patent: Aug. 4, 2015

(54) METHOD AND APPARATUS FOR PERFORMING PEPTIDE DIGESTION ON A MICROFLUIDIC DEVICE

(75) Inventors: Bahram Fathollahi, Palo Alto, CA (US); Javier A. Farinas, Los Altos, CA (US); Andrea W. Chow, Los Altos, CA (US); Stephane Mouradian, Menlo Park, CA (US)

(73) Assignee: Caliper Life Sciences, Inc., Hopkinton, MA (US)

( * ) Notice: Subject to any disclaimer, the term of this patent is extended or adjusted under 35 U.S.C. 154(b) by 1815 days.

(21) Appl. No.: 11/397,307

(22) Filed: Apr. 3, 2006

(65) Prior Publication Data

US 2006/0246533 A1  Nov. 2, 2006

Related U.S. Application Data

(60) Provisional application No. 60/667,608, filed on Apr. 1, 2005.

(51) Int. Cl.
*C12Q 1/37* (2006.01)
*G01N 33/543* (2006.01)
*G01N 33/68* (2006.01)

(52) U.S. Cl.
CPC ................ *G01N 33/6842* (2013.01)

(58) Field of Classification Search
CPC ....... B01L 7/525; B01L 3/50273; B01L 7/52; B01L 2200/10; B01L 2200/16; B01L 9/527; B01L 2300/087; B01L 3/5027; B01L 2200/027

USPC .......................................... 204/452
See application file for complete search history.

(56) References Cited

U.S. PATENT DOCUMENTS

| | | | |
|---|---|---|---|
| 5,538,897 A | 7/1996 | Yates, III | |
| 6,632,655 B1 | 10/2003 | Mehta et al. | |
| 6,783,647 B2 | 8/2004 | Culbertson | |
| 6,858,185 B1* | 2/2005 | Kopf-Sill et al. | 422/504 |
| 2001/0027918 A1* | 10/2001 | Parce et al. | 204/452 |
| 2001/0045358 A1* | 11/2001 | Kopf-Sill et al. | 204/452 |
| 2001/0049148 A1* | 12/2001 | Wolk et al. | 436/180 |
| 2002/0119482 A1* | 8/2002 | Nelson et al. | 435/6 |
| 2003/0089605 A1* | 5/2003 | Timperman | 204/450 |
| 2003/0186326 A1 | 10/2003 | Regnier | |
| 2004/0072251 A1* | 4/2004 | Anderson | 435/7.1 |
| 2004/0245102 A1 | 12/2004 | Gilbert | |
| 2005/0266582 A1* | 12/2005 | Modlin et al. | 436/164 |
| 2005/0277195 A1* | 12/2005 | Holmquist et al. | 436/37 |

OTHER PUBLICATIONS

Gao et al., Integrated microfluidic system enabling protein digestion, peptide separation, and protein identification, 2001, Anal Chem, 73: pp. 2648-2655.*

(Continued)

*Primary Examiner* — Bao Thuy L Nguyen
*Assistant Examiner* — Kyung Sung
(74) *Attorney, Agent, or Firm* — Cardinal Law Group

(57) ABSTRACT

The invention provides methods and apparatuses that allow a protein sample to undergo reduction, alkylation, and digestion in a continuous flow process carried out within a microfluidic device. Methods and apparatuses in accordance with the invention can be employed as part of an automated proteomics analysis carried out in an integrated proteomics system.

16 Claims, 6 Drawing Sheets

(56) References Cited

OTHER PUBLICATIONS

Wang et al., Integration of immobilized trypsin bead beds for protein digestion within a microfluidic chip incorporating capillary electrophoresis separations and an electrospray mass spectrometry interface, 2000, Rapid Com Mass Spec. 14: pp. 1377-1383.*

Jamil El-Ali, Suzanne Gaudet, Axel Gunther, Peter K. Sorger, and Klays F. Jensen, "Cell stimulus and lysis in a microfluidic device with segmented gas-liquid flow", Jun. 1, 2005, Analytical Chemistry, 77 (11).*

Kopp, Martin et al., "Chemical Amplification: Continuous-Flow PCR on a Chip", Science, May 15, 1998, pp. 1046-1048, vol. 280.

"Online Nano LC/Nanospray MS for the Analysis of Protein Digests", Application Note 518, LC Packings—a Dionex Company, 2002, 2 pp.

Astorga-Wells, Juan et al., "Multistep Microreactions with Proteins Using Electrocapture Technology", Anal. Chem. 2004, pp. 2425-2429, vol. 76 No. 9.

Li, Jianjun et al., "Application of Microfluidic Devices to Proteomics Research", Amer. Soc. for Biochem & Molecular Bio. (www.mcponline.org), 2002, pp. 157-168.

Wang, Can et al., "Integration of Immobilized Trypsin Bead Beds for Protein Digestion . . . ", Rapid Commun. Mass. Spectrom., 2000, pp. 1377-1383, vol. 14.

"Peptide Mapping by Reversed-Phase High-Performance Liquid Chromatography", Dionex Application Note 99, 1994, 6 pp.

"On-Line Clean-Up and Preconcentration of Protein Samples Prior to Nanoscale LC/MS/MS", App. Note 503, LC Packings—a Dionex Company, 2002, 2 pp.

"Proteomics Workflow With the UltiMate 3000", Dionex Company (printed Mar. 26, 2006 from http://www1.dionex.com/en-us/lp34836.html), 2005, 2 pp.

Nerelius, Charlotte et al., "Protein Reduction, Alkylation and Digestion in a CD Microlaboratory . . . ", Gyros AB (Uppsula, Sweden), 2003, 1 p.

* cited by examiner

METHOD AND APPARATUS FOR PERFORMING PEPTIDE DIGESTION ON A MICROFLUIDIC DEVICE

RELATED APPLICATIONS

The present application claims priority to U.S. Provisional Patent Application Ser. No. 60/667,608, filed Apr. 1, 2005, entitled "Method and Apparatus for Performing Peptide Digestion on a Microfluidic Chip", the contents of which are herein incorporated by reference.

TECHNICAL FIELD

The present invention relates to methods and apparatuses for the analysis of proteins. More particularly, embodiments of the present invention are directed toward the enzymatic digestion of proteins within a microfluidic device.

BACKGROUND OF THE INVENTION

Proteomics is a branch of biotechnology concerned with applying the techniques of molecular biology, biochemistry, and genetics to analyze the structure, function, and interactions of the proteins encoded by the genes of an organism. The term proteomics is somewhat analogous to the term genomics in that proteomics is the study of the proteome, the entire complement of proteins in a given biological organism at a given time, while genomics is the study of the genome, the genetic make-up of an organism. Even though the proteome of an organism is the product of that organism's genome, the proteome is larger than the genome, especially in eukaryotes, in the sense that there are more proteins than genes. This is because the genome of an organism is a rather constant entity, while the corresponding proteome differs from cell to cell and is constantly changing through its biochemical interactions with the genome and the environment. A single organism will have radically different protein expression in different parts of its body, in different stages of its life cycle and in different environmental conditions. For example, results from the Human Genome Project indicate that there are far fewer protein-coding genes in the human genome than there are proteins in the human proteome (~22,000 genes vs. ~400,000 proteins). The large number of proteins relative to the number of genes encoding those proteins results from mechanisms such as the alternative splicing of transcripts and the post-translational modification of proteins. There is an increasing interest in proteomics, primarily because proteins are involved in virtually every cellular function, control every regulatory mechanism and are modified in disease (as a cause or effect).

Proteomics typically involves the analysis of the proteins contained in a biological sample, such as a cell lysate. Methods of analyzing the proteins in a biological sample are often grouped into two categories: top-down methods and bottom-up methods. Top-down methods involve the characterization of the intact proteins in the sample, while bottom-up methods involve breaking the proteins in the sample into a number of component peptides, and then determining the identities of the those peptides. An advantage of top-down methods is that they can identify properties of intact proteins, such as whether the protein is phosphorylated or unphosphorylated, that cannot be detected if the proteins are broken down into peptides. A disadvantage of top-down methods is that they often unable to effectively identify individual proteins. Even though bottom-down methods are more effective in identifying proteins, they cannot be applied effectively when there are a large number of proteins in the sample. Consequently, many proteomics analyses involve a combination of top-down and bottom-up methods.

In an analysis employing both top-down and bottom down components, the role of the top-down component is typically to segregate the individual proteins in a biological sample. The traditional method of segregating a mixture of proteins is two-dimensional gel electrophoresis (2-DE). In a standard 2-DE process, a biological sample containing a mixture of proteins is placed on a separation gel, which is usually a polyacrylamide matrix. The proteins on the gel are separated according to differences in a first property, typically mass, along a first direction. The proteins in the gel are then separated according to differences in a second property, typically isoelectric point, along a second direction that is orthogonal to the first direction. The two-dimensional separation process produces one or more protein "spots" distributed across a 2-D surface of the gel. Unfortunately, 2-DE methods are only effective in isolating the most abundant proteins in a sample. This lack of sensitivity primarily results from the fact that high abundance proteins mask the presence of low abundance proteins. Even if low-abundance proteins are effectively isolated from higher abundance proteins during 2-DE, the subsequent analysis of low-abundance proteins by mass spectrometry (MS) is hindered by the fact that the amount of protein required for identification by MS is near the detection limits of the most sensitive methods used to visualize the protein spots on 2-DE gels, and the fact that those gels can produce a significant amount of background during MS analysis.

Multi-dimensional column separations offer many advantages over traditional 2-DE methods, including a higher separating power, and reduced sample contamination and loss. A multi-dimensional column separation process involves sequentially subjecting a mixture of proteins to two or more separation processes to segregate the individual proteins. Those separation processes can include size exclusion chromatography, reversed phase High Performance Liquid Chromatography (RP-HPLC), ion-exchange chromatography, and capillary electrophoresis. For example, in the Ultimate™ 3000 integrated proteomics system manufactured and sold by the Dionex Corporation of Sunnyvale, Calif. (www.dionex.com), the proteins in a cell lysate are first separated by ion-exchange chromatography, producing a series of fractions, each of which containing one or more proteins. Each fraction is then subject to a RP-HPLC process, further refining the fractions. The number of proteins in each further refined fraction is typically low enough so that each of those fractions can be subject to a bottom-up analysis.

A bottom-up analysis of a protein sample requires that the proteins in the sample be broken down into a number of component peptides. The process of breaking up proteins into peptide components involves several steps, which typically include the reduction, alkylation, and digestion of the proteins. The reduction step reduces disulfide bonds within the protein. The alkylation step alkylates cysteine residues, and prevents the protein from assuming its native conformation. The reduction and alkylation steps allow the subsequent digestion step to be better controlled and more efficient. In the digestion step, proteins are broken up into peptide fragments by means of an endopeptidase enzyme that specifically cleaves the bonds between certain peptides in a protein. The most commonly used enzyme used for digestion is trypsin, which very specifically cleaves peptide bonds on the carboxyl side of lysine and arginine residues. As an example, bovine fetuin is a protein that is 341 amino acid residues in length. When bovine fetuin is digested with trypsin, it is broken up into twenty-five separate peptides that range in length from two to eighteen amino acid residues.

After a protein sample is digested, the resulting peptide fragments are subjected to analytical techniques that can enable the identification of the protein or proteins within the sample. One such process is peptide mass fingerprinting (PMF). The basic idea behind PMF is that the collection of peptides produced by digesting a protein constitutes a unique identifier or "fingerprint" of the protein. A protein's fingerprint is produced by accurately measuring the masses of the peptide fragments produced by digestion with a mass spectrometer such as MALDI-TOF or ESI-TOF. The PMF technique is described in detail in U.S. Pat. No. 5,538,897. An alternative method of analyzing a protein that has been digested is tandem mass spectrometry. A tandem mass spectrometer is capable of multiple rounds of mass spectrometry. For example, one mass analyzer can isolate one peptide fragment from many entering the mass spectrometer. A second mass analyzer then stabilizes the peptide ions while they collide with a gas, causing them to fragment by collision-induced dissociation (CID). This fragmentation process primarily gives rise to cleavage products that break along peptide bonds. Because of this simplicity in fragmentation, it is possible to use the observed masses of the cleavage products to match with a database of predicted masses for one of many given peptides. A third mass analyzer then catalogs the fragments produced from the peptides. Tandem MS can also be done in a single mass analyzer over time as in a quadrupole ion trap. A third alternative method of identifying proteins uses a combination of high-pressure liquid chromatography (HPLC) and MS. In this third method, a peptide mixture resulting from digestion of a protein mixture is fractionated by one or two steps of liquid chromatography. The eluent from the chromatography stage can be either directly introduced to the mass spectrometer through electrospray ionization, or laid down on a series of small spots for later mass analysis using MALDI.

In the current state of the art, there are a number of difficulties associated with proteomics analyses employing digestion. One difficulty is that when trypsin digestion is carried out in solution the digestion process can be extremely time consuming. For example, digestion processes carried out in a solution contained within a well of a multiwell plate often take several hours to complete. The rate of digestion can be increased by increasing the in-solution concentration of the trypsin enzyme, but high concentrations of trypsin can lead to autolysis of the enzyme, which produces large amount of contaminant peptides. Autolysis can be avoided by immobilizing the trypsin enzyme on a solid support, allowing the trypsin to be present at high enough levels so that the digestion process takes minutes instead of hours. For example, Applied Biosystems of Foster City manufactures and sells Poroszyme® cartridges, which contain trypsin immobilized on polystyrene beads. Trypsin digestion can be carried out in approximately five minutes by flowing a protein sample through a Poroszyme cartridge. A similar product is the StyrosZyme™ TPCK-Trypsin column manufactured by OraChrom, Inc. of Woburn, Mass. Although the use of cartridges containing immobilized trypsin can reduce the time it takes to digest a protein sample, it is impossible to process multiple samples in parallel using existing cartridge technology. Furthermore, existing cartridge products are not capable of performing the preliminary reduction and alkylation steps. These shortcomings of existing cartridge products hinder their integration into automated proteomics systems designed to process a large numbers of protein samples. Indeed, many currently available automated proteomics systems such as the Ultimate™ 3000 integrated proteomics system still perform reduction, alkylation, and digestion in multiwell plates, in spite of the time-consuming in-solution digestion process, because the use of multiwell plates allows a large number of samples to processed in parallel.

As an alternative to cartridges, immobilized trypsin can be placed within the channels of a microfluidic device. Microfluidic devices contain channels having at least one linear interior dimension, such as depth or radius, of less than 1 mm. It is possible to create microscopic equivalents of bench-top laboratory equipment such as beakers, pipettes, incubators, electrophoresis chambers, and analytical instruments within the channels of a microfluidic device. Since it is also possible to combine the functions of several pieces of equipment on a single microfluidic device, a single microfluidic device perform a complete analysis that would ordinarily require the use of several pieces of laboratory equipment. A microfluidic device designed to carry out a complete chemical or biochemical analyses is commonly referred to as a micro-Total Analysis System (β-TAS) or a "lab-on-a chip". Thus it should be possible to perform several of the processes required for the analysis of a protein within a single microfluidic device. For example, researchers at the University of Alberta have designed a microfluidic device in which a protein sample is digested by flowing the sample through a packed bed of beads coated with immobilized trypsin, the component peptides produced by digestion are separated by capillary electrophoresis, and finally the separated peptides are introduced into a mass spectrometer. Wang et al., RAPID COMMUN. MASS. SPECTROM. 14, 1377-1383 (2000). Presumably the samples introduced into the microfluidic device designed by Wang et al. must have been already reduced and alkylated since the device is not configured to perform reduction and alkylation. The exclusion of the reduction and alkylation steps from the device described by Wang et al. may result from the difficulties associated with performing the three steps of reduction, alkylation, and digestion on a single microfluidic device. Among those difficulties are that those three steps take different amounts of time, require different chemical environments, and are optimally performed at different temperatures. The fact that the steps take different amounts of time makes it difficult to perform those three steps sequentially in a continuous flow manner on a single microfluidic device. Some researchers have sidestepped this issue by immobilizing a protein sample at a particular location within a channel in a microfluidic device by either binding the proteins in the sample to a derivatized surface or by using the combination of an electric field and hydrodynamic flows to hold the proteins in place. See e.g. Astorga-Wells et al., ANAL. CHEM. 76, 2425-2429 (2004). Once a protein sample is immobilized in a channel, the various reagents required for reduction, alkylation, and digestion are sequentially flowed through the channel. After those three processes are complete, the resulting peptides are allowed to exit the channel. Although immobilizing a protein sample does allow the reduction, alkylation, and digestion processes to be carried out on a single microfluidic device, the structures and equipment required to immobilize the sample increase the cost and complexity of the microfluidic device.

It is thus an object of the present invention to carry out the reduction, alkylation, and digestion processes in a microfluidic device in a manner that overcomes the previously described shortcomings. These and further objects will be more readily appreciated when considering the following disclosure and appended claims.

SUMMARY OF THE INVENTION

The invention provides methods and apparatuses that allow a protein sample to undergo reduction, alkylation, and digestion in a continuous flow process carried out within a single microfluidic device. Methods and apparatuses in accordance with the invention can be employed as part of an automated proteomics analysis carried out in an integrated proteomics system.

DETAILED DESCRIPTION OF THE INVENTION

A lab-on-a-chip type microfluidic device, which can simply be referred to as a "chip", is typically used as a replaceable component, like a cartridge or cassette, within an instrument. The chip and the instrument form a complete microfluidic system. The instrument can be designed to interface with the microfluidic devices designed to perform different assays, giving the system broad functionality. For example, the commercially available Agilent 2100 Bioanalyzer system can be configured to perform different types of assays—namely DNA, RNA, protein, and cell assays—by simply placing the appropriate type of chip into the instrument.

In a typical microfluidic system, all of the microfluidic channels are in the interior of the chip. The instrument can interface with the chip by performing a variety of different functions: supplying the driving forces that propel fluid through the channels in the chip, monitoring and controlling conditions (e.g., temperature) within the chip, collecting signals emanating from the chip, introducing fluids into and extracting fluids out of the chip, and possibly many others. The instruments are typically computer controlled so that they can be programmed to interface with different types of chips, and to interface with a particular chip in such a way as to carry out a desired analysis.

Microfluidic devices designed to carry out complex analyses will often have complicated networks of intersecting channels. Performing the desired assay on such chips will often involve separately controlling the flows through certain channels. Even when the flows through several channels in a microfluidic device are all propelled by the same driving force, the flow rates through those channels can be separately controlled by varying the geometries of the channels. Techniques for controlling the flow through a series of channels by varying the channel geometry are described in U.S. Pat. Nos. 6,062,261; 6,858,185; and 7,001,716.

One of the major impediments to the widespread adoption of microfluidic technology is the cost of manufacturing a microfluidic device, or chip. Issues related to cost arise because materials that are inexpensive to process into chips, such as many common polymers, are not necessarily chemically inert or optically transparent enough to be suitable for many applications. To address the cost issue, technology has been developed that allows microfluidic chips fabricated from more expensive materials to be reused, lowering the cost per use. See U.S. Published Application No. 2005/0019213. If a chip can be manufactured cheaply enough, the chip can be disposed of after a single use. A disposable chip would eliminate the problems associated with cross-contamination from previously processed samples.

Figure 1:
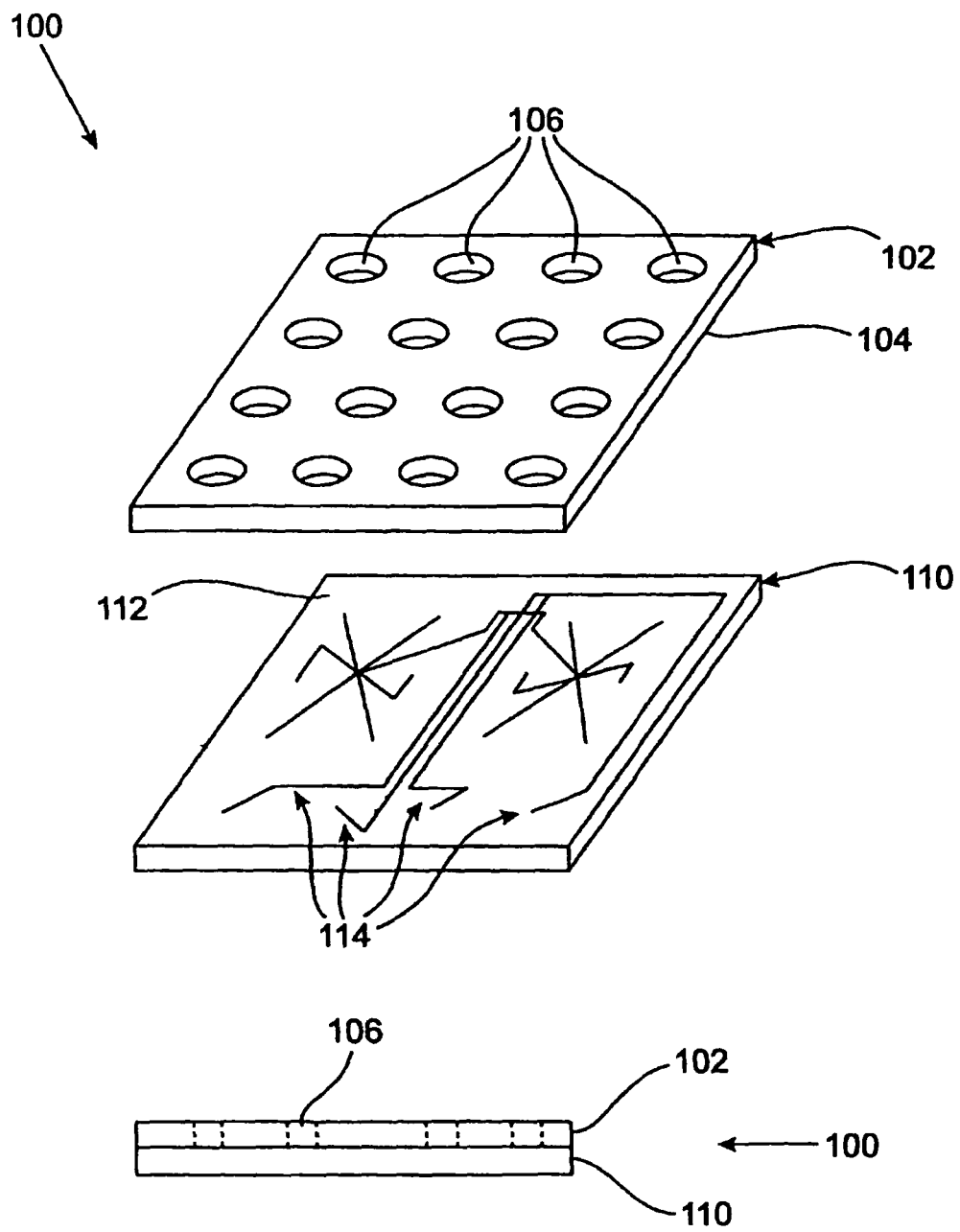
FIG. 1 is a representation of a generic microfluidic device.

As noted previously, embodiments of the present method are directed toward carrying out the reduction, alkylation, and digestion of a plurality of protein samples in a single microfluidic device. FIG. 1 illustrates is a schematic representation of a typical microfluidic device that can be used to carry out methods in accordance with the invention. The top portion of FIG. 1 shows an exploded view of the device 100, which is consists of two planar substrates 102, 110, while the bottom portion of FIG. 1 shows a side view of the assembled device 100 after the two planar substrates 102, 110 have been bonded together. Structures such as channels or chambers within the interior of the assembled microfluidic device 100 are formed by fabricating a pattern of grooves and trenches 114 on a surface 112 of one substrate 110, and bonding a surface 104 of the second substrate 102 onto the patterned surface 112. When the substrates are bonded together, the grooves and trenches 114 are enclosed, forming channels and chambers within the interior of the assembled device 100. Access to those channels and chambers is provided through ports 106, which are formed by simply fabricating holes in the upper substrate 102. The ports are positioned to communicate with specific points of the channels. For example, the ports 106 are positioned to communicate with the termini of the channels formed by enclosing grooves 114. The ports 106 can be used to introduce fluid into or extract fluids out of the channels of the device 100, or to allow driving forces such as electricity or pressure to be applied to the channels to control flow throughout the network of channels and chambers.

A variety of substrate materials may be employed to fabricate a microfluidic device such as device 100 in FIG. 1. Typically, because the devices are microfabricated, since some structures such as the grooves or trenches will have a linear dimension of less than 1 mm, it is desirable that the substrate material be compatible with known microfabrication techniques such as photolithography, wet chemical etching, laser ablation, reactive ion etching (RIE), air abrasion techniques, injection molding, LIGA methods, metal electroforming, or embossing. Another factor to consider when selecting a substrate material is whether the material is compatible with the full range of conditions to which the microfluidic devices may be exposed, including extremes of pH, temperature, salt concentration, and application of electric fields. Yet another factor to consider are the surface properties of the material. The surface properties of the interior channel surfaces determine how the channel surface chemically interacts with materials flowing through the channels, and those properties will also affect the amount of electroosmotic flow that will be generated if an electric field is applied across the length of the channel. Since the surface properties of the channel are so important, techniques have been developed to either chemically treat or coat the channel surfaces so that those surfaces have the desired properties. Examples of processes used to treat the surfaces of microfluidic channels can be found in U.S. Pat. Nos. 5,885,470; 6,841,193; 6,409,900; and 6,509,059. Methods of bonding two substrates together to form a completed microfluidic device are also known in the art. See, for example, U.S. Pat. Nos. 6,425,972 and 6,555,067.

Materials normally associated with the semiconductor industry are often used as microfluidic substrates since microfabrication techniques for those materials are well established. Examples of those materials are glass, quartz, and silicon. In the case of semiconductive materials such as silicon, it will often be desirable to provide an insulating coating or layer, e.g., silicon oxide, over the substrate material, and particularly in those applications where electric fields are to be applied to the device or its contents. The microfluidic devices employed in the Agilent Bioanalyzer 2100 system are fabricated from glass or quartz because of the ease of microfabricating those materials, and because those materials are generally inert in relation to many biological compounds. Microfluidic devices can also be fabricated from polymeric materials such as polymethylmethacrylate (PMMA), polycarbonate, polytetrafluoroethylene (TEFLON™), polyvinylchloride (PVC), polydimethylsiloxane (PDMS), polysulfone, polystyrene, polymethylpentene, polypropylene, polyethylene, polyvinylidine fluoride, ABS (acrylonitrile-butadiene-styrene copolymer), cyclic-olefin polymer (COP), and cyclic-olefin copolymer (COC). Such polymeric substrate materials are compatible with a number of the microfabrication techniques described above. Since microfluidic devices fabricated from polymeric substrates can be manufactured using low-cost, high volume processes such as injection molding, polymer microfluidic devices could potentially be less expensive to manufacture than devices made using semiconductor fabrication technology. Nevertheless, there are some difficulties associated with the use of polymeric materials for microfluidic devices. For example, the surfaces of some polymers interact with biological materials, such as proteins. So even though microfluidic devices may be fabricated from a variety of materials, there are tradeoffs associated with each material choice.

Figure 2:
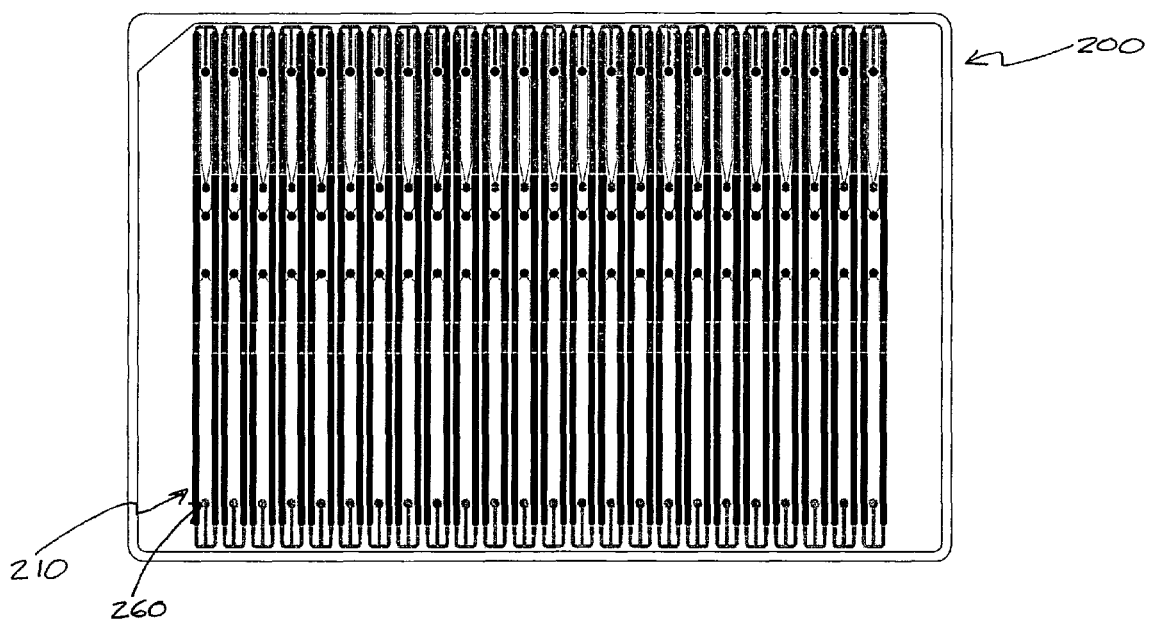
FIG. 2 is a schematic representation of a microfluidic device in accordance with the invention.
Figure 3:
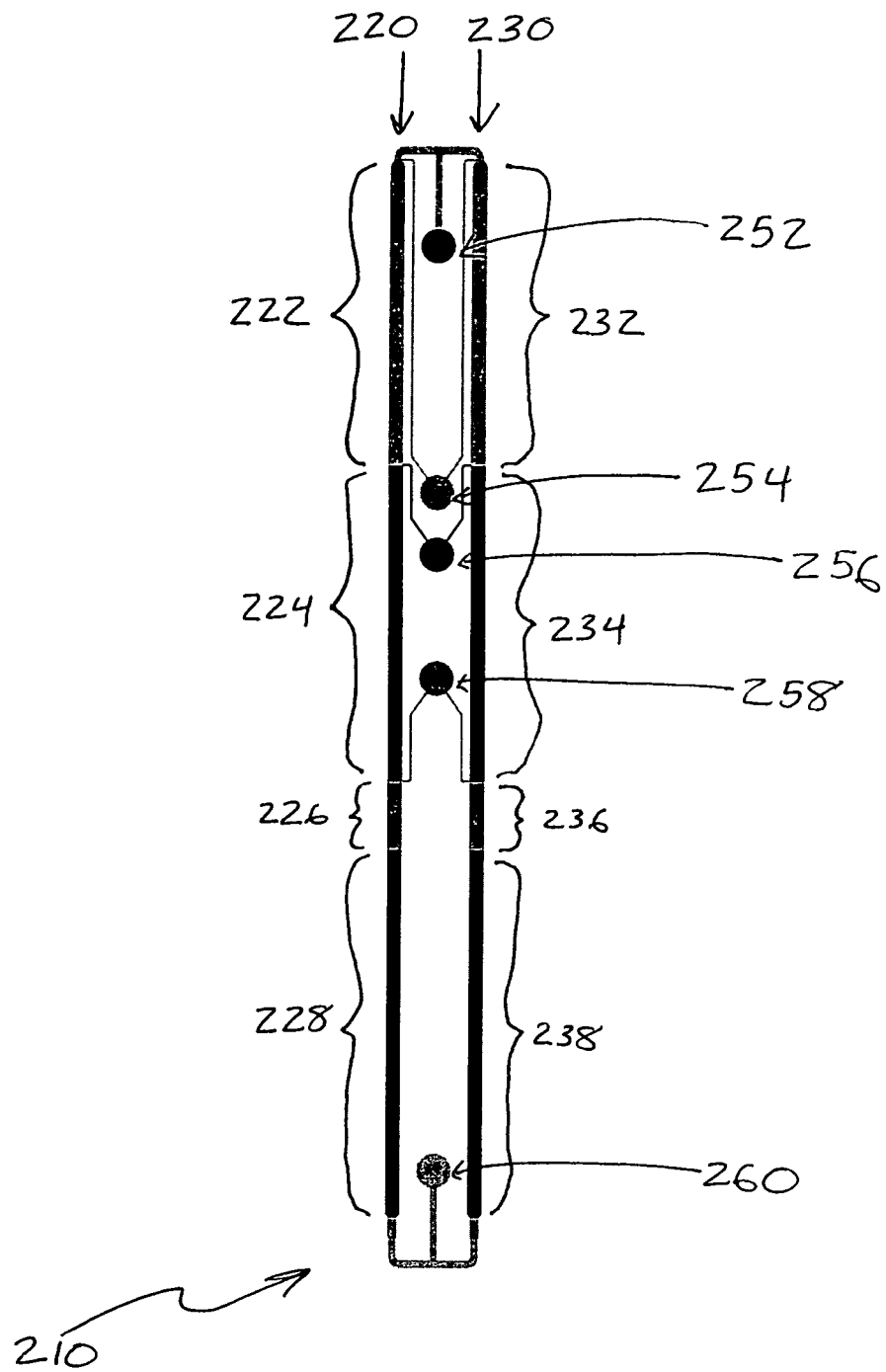
FIG. 3 is a more detailed view of a portion of the microfluidic device in FIG. 2.

The exact channel configuration of a microfluidic device in accordance with the invention is shown in FIG. 2. The top-down view of the device 200 in FIG. 2 shows that the device contains twenty-four identical fluid networks 210. A detailed view of one of the networks 210 is shown in FIG. 3. Each fluid network 210 contains two primary channels 220 and 230, each of which consists of four segments 222,224,226,228 and 232,234,236,238 respectively. The two primary channels 220,230 are in fluid communication with five ports 252,254, 256,258,260. These ports correspond to the ports 106 described in FIG. 1. One of the five ports 252 in the fluid network 210 serves as a reservoir for the protein sample to be processed. Three of the other ports 254,256,258 serve as reservoirs for reagents used during the processing of the sample. The fifth and final reservoir 260 serves as a waste reservoir. In order to move fluids through the channels in the network 210, a negative (i.e. sub-atmospheric) pressure is applied to reservoir 260, while the remaining reservoirs are left open to the atmosphere. The application of the negative pressure to reservoir 260 creates pressure gradients that will cause fluid to flow from the sample and reagent reservoirs 252,254,256,258 through channels (not numbered) that fluidly connect those reservoirs to the two main channels 220 and 230. Fluid flow can be simultaneously initiated in each of the twenty-four networks 210 in FIG. 2 by simultaneously applying a negative pressure to the waste reservoirs in each of the networks 210. Methods and apparatuses for applying negative pressures to reservoirs, and for simultaneously applying negative pressure to corresponding reservoirs in a plurality of fluid networks, are known in the art. For example, methods and apparatuses compatible with embodiments of the invention are described in U.S. Pat. No. 6,488,895.

Figure 4:
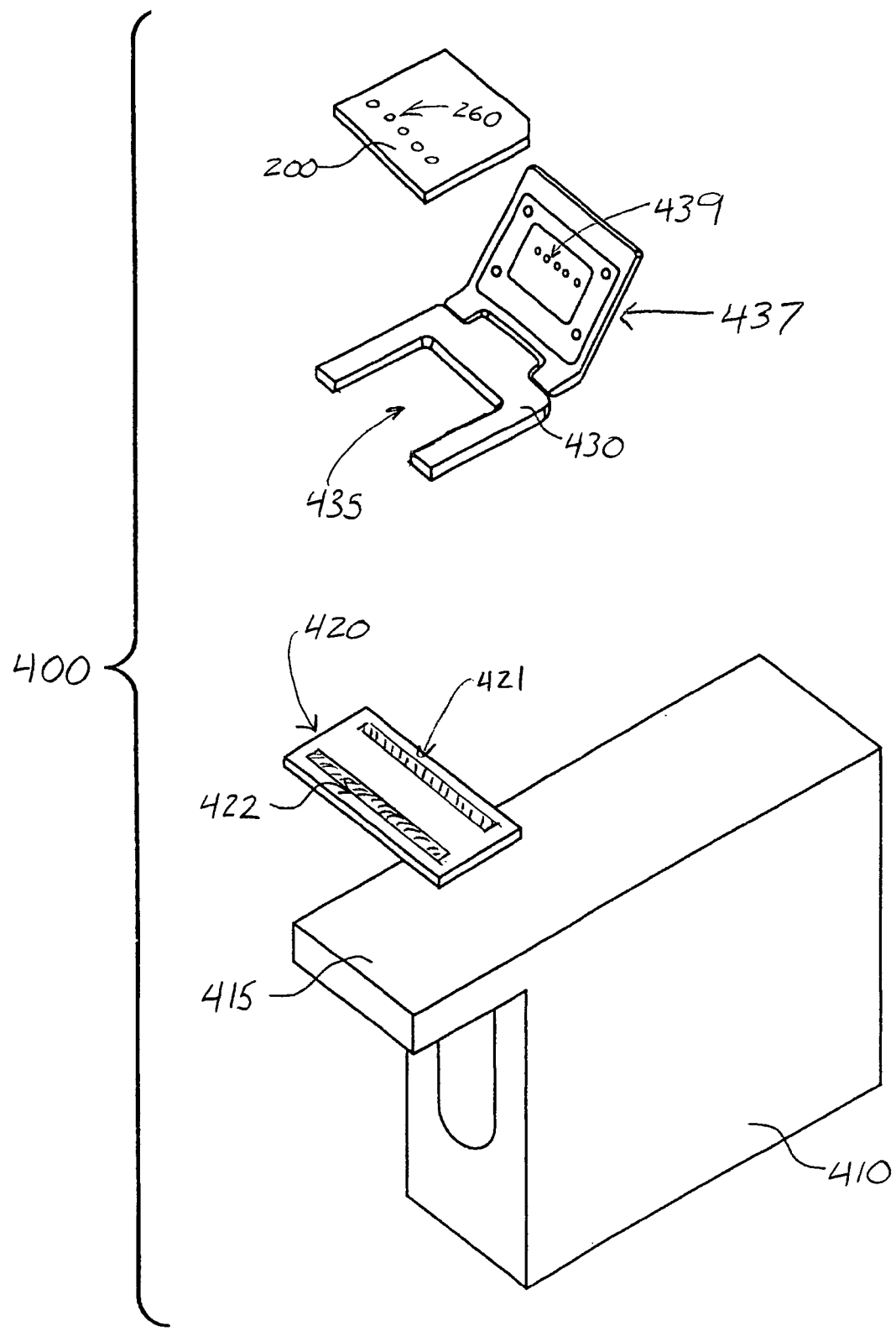
FIG. 4 is a schematic representation of a microfluidic system in accordance with the invention.

The microfluidic device 200 is typically interfaced with an instrument that provides the pressure driving forces that propel fluid through the channels in the chip, and that controls the temperature within the channels of the chip. An exploded view of an instrument in accordance with the invention is shown in FIG. 4. The microfluidic system comprises a microfluidic device or chip 200, an adapter plate 430 configured to receive the chip, a heating plate 420 that is placed in thermal contact with the chip 200, an interface region 415 that provides an interface between the main body 410 of the instrument and both the heating plate 420 and the adapter plate 430. The adapter plate comprises a recessed region 435 that holds the chip 200 in place during operation of the device. When the chip 200 is placed within the recessed region 435, a rotatable lid 437 can be closed, placing pressure outlet ports 439 in physical contact with the waste reservoirs 260 on the chip 200. Upon closing of the lid 437, the pressure outlet ports 439 are able to transmit a negative pressure generated by a pressure source, such as a pneumatic pump, contained within the instrument body 410 to the waste reservoirs 260 on the chip 200. The chip embodiments shown in FIGS. 2 and 3 allow the pressure from a single pressure source to be distributed, e.g. via a manifold, to all of the waste reservoirs 260 on a chip 200. The heating plate 420 in FIG. 4 comprises two separate temperature zones 421,422 that are maintained at different temperatures when the system 400 is in operation. The presence of the two different temperature zones 421,422 on the heating plate allows two different regions of the chip to be maintained at two different temperatures when the system 400 is in operation. Methods for controlling different regions of a microfluidic device at different temperatures are well known in the art. See e.g. Kopp et al., SCIENCE 280 (15 May 1998).

The first step in performing methods in accordance with the invention is to fill each of the appropriate reservoirs 252, 254,258 in the twenty-four parallel networks 210 on the microfluidic device 200 with the appropriate sample or reagent. A protein sample to be reduced, alkylated, and digested is placed in sample reservoir 252. Since a different protein sample can be placed in the sample reservoir 252 of each different network, the embodiment shown in FIG. 2 is capable of processing twenty-four protein samples simultaneously. The first reagent reservoir 254 is filled with a first reagent that will reduce the protein sample. The second reagent reservoir 256 is filled with a second reagent that will alkylate the protein sample. The third reagent reservoir 258 is filled with a reagent that neutralizes the alkylation reagent so that the alkylation reagent does not inhibit digestion of the protein.

The next step in methods according to the invention is placing the filled chip 200 into the recess 435 in adapter 430, and closing the lid 437 so that a negative pressure generated in the instrument body 410 can be transmitted to the waste reservoirs 260 on the chip. In the embodiment of FIGS. 2-4, the channel segments 222,232 in all twelve networks are in thermal contact with the first temperature zone 421, while the channel segments 228,238 in all twelve networks are in thermal contact with the second temperature zone 422. First temperature zone 421 is maintained at a temperature that causes the temperature within channel segments 222,232 to be maintained at a first temperature. Similarly, second temperature zone 422 is maintained at a temperature that causes the temperature within channel segments 228,238 to be maintained at a second temperature. The transmission of the negative pressure to the waste reservoir 260 in each network 210 causes the fluids contained in reservoirs 252, 254, 256, and 258 to flow through channels 220 and 230 into waste reservoir 260. As the protein sample flows from sample reservoir 252 into channels 220 and 230, the sample mixes with the first reagent flowing out of the first reagent reservoir 252 at the beginning of channel segments 222 and 232. In the illustrated embodiment, the first reagent is a reduction reagent. The reduction reagents used in standard protein analyses can be also be employed in embodiments of the invention. Perhaps the most common reagent used to reduce protein samples is dithiothreitol (DTT). See, e.g. the protocols listed on the website of the University of Western Ontario Biological Mass Spectrometry Laboratory (www.biochem.uwo.ca). Other reducing agents, such as tris(2-carboxyethyl) phosphine (TCEP) can be employed in alternative embodiments of the invention. The relative concentrations of reduction reagent and protein can be the same relative concentrations used in existing reduction protocols. It is known in the art that the reduction process takes less time if it is carried out at an elevated temperature. Accordingly, the first temperature within channel segments 222,232 is above room temperature. The first temperature, for example, could be 37° C., or alternatively 50° C. A standard reduction protocol can be completed at 37° C. in about one-fourth the time required to complete the protocol at room temperature. The reduction reaction takes place as the mixture of reduction reagent and protein sample flows through channel segments 222,232. Note that the continuous application of the negative pressure to waste reservoir 260 produces a continuous flow of protein sample and reagent through channel segments 222,232. The time period over which the reduction reaction occurs is the residence time of the protein sample/reduction reagent mixture in channel segments 222,232. The second reagent stored in reservoir 256 is added to the mixture when the mixture enters the second channel segments 224,234. In the illustrated embodiment, the second reagent is an alkylation reagent. The alkylation reagents used in standard protein analyses can be also be employed in embodiments of the invention, and in the same relative concentrations as in standard analytes. Perhaps the most commonly used alkylation reagent is iodoacetic acid. Other alkylation reagents that may be employed in embodiments of the invention include iodoacetamide and vinylpyridine. The amount of time over which the alkylation reaction occurs is equal to the residence time of the mixture in channel segments 224,234. The third reagent in the third reagent reservoir 258 is added to the mixture in order to quench the alkylation reagent so that the alkylation reagent does not inhibit digestion. In accordance with standard protocols, a thiol such as dithiothreitol can serve as the quenching reagent. The time period over which the quenching reaction occurs is equal to the residence time of the mixture in segments 226 and 236. The last segments 228,238 of channels 220 and 230 contain trypsin immobilized on a solid support. Accordingly, proteins in the mixtures flowing through channels 220 and 230 are digested as the mixture flows through channel segments 228,238. As previously discussed, channel segments 228,238 are maintained at a second temperature as a result of their thermal contact with second temperature zone 422. The second temperature is typically around 37° C. Commercially available forms of immobilized trypsin may be employed in embodiments of the invention. For example, Pierce Biotechnology of Rockford Ill. (www.piercenet.com) sells trypsin treated with TPCK immobilized on agarose beads. The beads containing the immobilized trypsin are placed into channel segments 228,238 in such a manner as to form a packed bed. Methods of manipulating beads in microfluidic channels are known in the art. See e.g. U.S. Pat. No. 6,632,655. After exiting channel segments 228,238, the digested protein sample flows into waste reservoir 260.

As one skilled in the art of microfluidics would recognize, the residence of a fluid in a channel segment is a function of the fluid properties (i.e. viscosity, density), the channel geometry (i.e. cross-sectional shape, cross-sectional area, and length), and the magnitude of the driving force propelling the fluid through the channel segment. Since the same driving force is applied to all four segments 222,224,226,228 of channel 220, as well as all four segments 232,234,236,238 of channel 230, and since the properties of the fluids flowing through those various segments do not significantly vary, the residence time in each of the various channel segments is basically determined by the geometry of the channel segments. Therefore the amount of time the continuous streams of fluid flowing through channels 220 and 230 spend in each segment of those channels is determined by the channel geometries of those segments. Thus by varying the geometries of the various channel segments through which a continuous stream of fluid flows, the fluid can spend different amounts of time within each of those segments.

Figure 5:
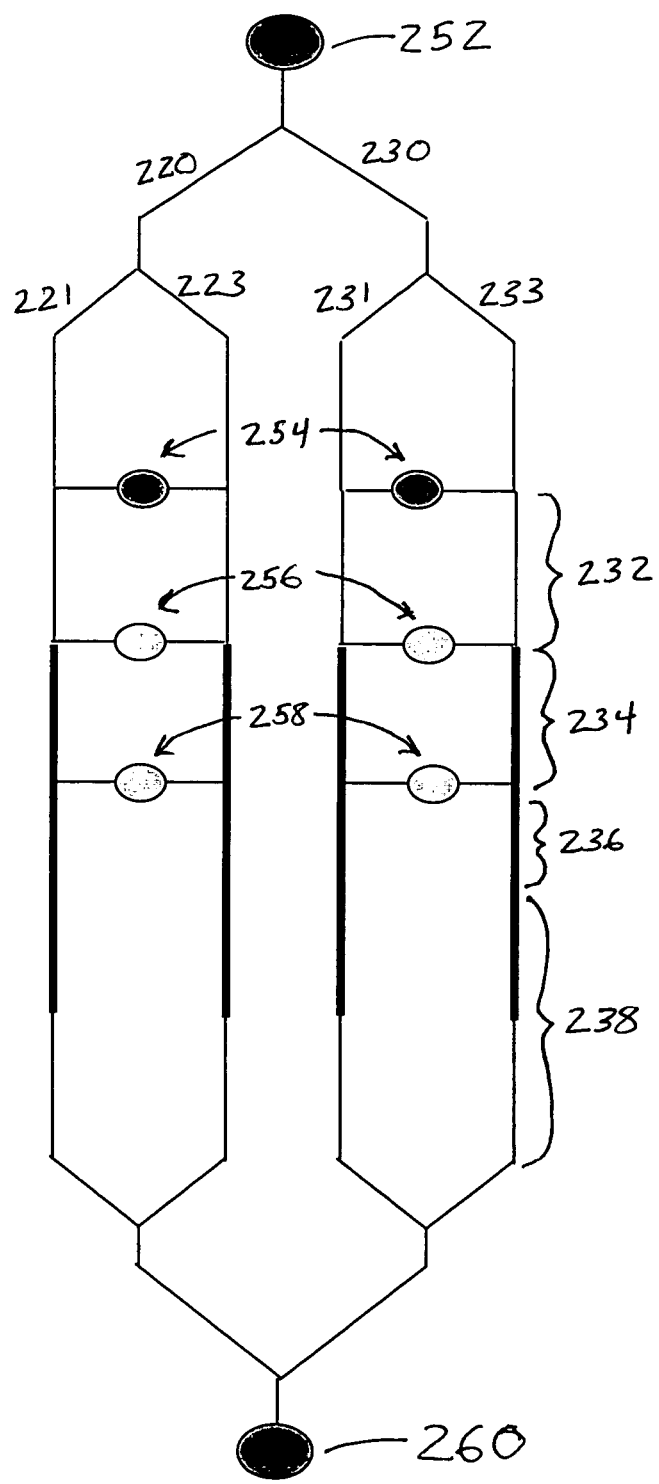
FIG. 5 is a schematic representation of a portion of the channel geometry in a microfluidic device in accordance with the invention.

In the embodiments shown in FIGS. 2 and 3, the flow of protein sample is distributed between two different channels 220 and 230. Distributing flow among multiple microfluidic channels allows more sample to be processed without requiring that the channel dimensions be increased beyond microfluidic (i.e. <1 mm) dimensions. Microfluidic channels offer a variety of advantages over larger channels. For example, microfluidic scale channels can be fabricated on inexpensive substrates using well-established fabrication technologies, and the high surface-to-volume ratios of microfluidic channels provide improved heat transfer and temperature control. To increase the rate at which a protein sample is processed, the flow of sample can be distributed to more than two channels. The embodiment in FIG. 5 distributes the flow of sample from sample reservoir 252 into four channels 221,223,231, 233. The embodiment of FIG. 5 contains reservoirs and channel segments that correspond exactly to the reservoirs and channel segments described in relation to the embodiment shown in FIGS. 2 and 3.

Figure 6:
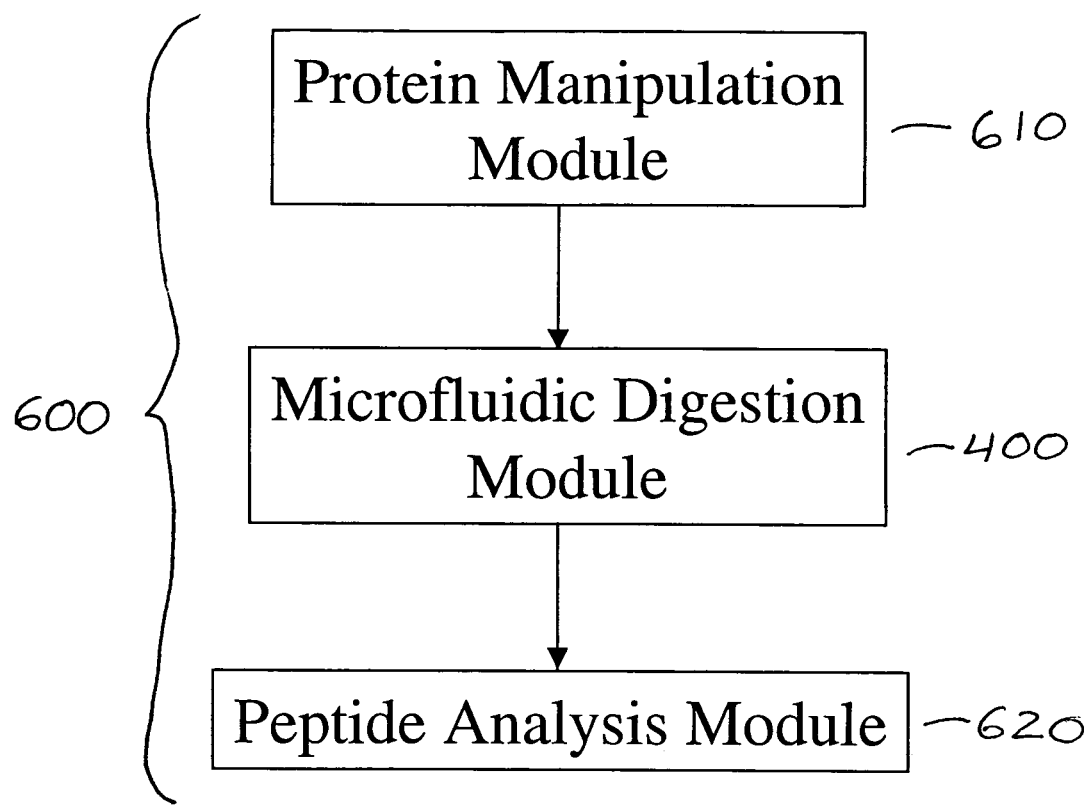
FIG. 6 is a schematic representation of an automated proteomics analysis system comprising a microfluidic system in accordance with the invention.

A microfluidic system capable of reducing, alkylating, and digesting a protein sample can be a component of an integrated proteomics system. A schematic representation of an integrated proteomics systems comprising a microfluidic system 400 in accordance with the invention is shown in FIG. 6. The protein manipulation module 610 and peptide analysis module 620 can correspond to components of existing integrated proteomics systems such as the Ultimate 3000. For example, the protein manipulation module 610 could subject a biological sample, such as a cell lysate, containing a mixture of proteins to multi-dimensional column separation processes in order to divide the mixture of proteins in the sample into a number of fractions. The protein manipulation module 610 could also perform other processes, such as subjecting the fractions to a reverse-phase cleanup process. It is desirable that the fractions generated by the protein manipulation module 610 be transferred to the microfluidic digestion module in an automated process. If the sample reservoirs 252 in the microfluidic device 200 portion of the microfluidic system 400 are arranged with the same spacing as the wells in a standard format multiwell plate, then standard liquid handling equipment could be used to transfer the fractions generated by the protein manipulation module 610, which are typically stored in standard format multiwell plates, into the sample reservoirs 252 in the microfluidic device. The standard format for multiwell plates are promulgated by the Microplate Standards Development Committee of the Society for Biomolecular Sciences (SBS). The most common formats contain 96 wells in an 8×12 array, or 384 wells arrayed in 12×32 array. Thus if the fractions output of the protein manipulation module 610 are stored in a 96 well plate, many standard pieces of liquid handling equipment designed to transfer liquids in and out 96 well plate contain a row of eight pipettes designed to process an entire row of wells at once. Accordingly, a microfluidic device containing eight sample wells 252 that are separated by the center-to-center distance between the wells in a row of a 96-well plate could receive the row of eight pipettes in standard liquid handling equipment. Similarly, it is also desirable that the waste wells 260 also be arranged to be compatible with standard liquid handling equipment so that such equipment can transfer digested samples from the microfluidic digestion module into the peptide analysis module 620.

EXAMPLE

In a specific implementation of the microfluidic devices shown in FIGS. 2 and 3, the temperature of channel segments 222 and 232 is set to 50° C., while the temperature in channel segments 228 and 238 is set to 37° C. The temperature of the other channel segments is not controlled. The protein sample place in sample reservoir 252 contains protein at a concentration of 1 mg/mL in a solution of 7M guanidine-HCl in 100 mM ammonium bicarbonate buffer. The first reagent reservoir 254 contains 1M dithiothreitol, the second reagent reservoir contains 1M iodoacetic acid, and the third reagent reservoir contains 1M dithiothreitol. The flow through channels 220 and 230 is driven by applying a pressure of −4.5 psig to reservoir 260. The first channel segments 222 and 232 are 40 mm in length, 150 μm deep, and 700 μm wide. This results in a residence time of approximately 270 seconds for the fluid flowing through those channel segments 222 and 232. The second and third channel segments 224,234 and 226,236 are 150 μm deep and 1 mm wide. The second channel segments are 50 mm in length, producing a residence time of approximately 260 seconds, while the third channel segment is 11.5 mm in length, producing a residence time of approximately 60 seconds. The fourth channel segments 228 and 238 are 96 mm in length, 150 μm deep, and 700 μm wide. This provide for a residence time of approximately 300 seconds. Note that the residence time in the fourth channel is reduced by the presence of the beads in the channel. The small channels that connect the three reagent reservoirs to channels 220 and 230 are approximately 10 μm deep and 150 μm wide. Since those channels have a small cross-sectional area compared to the other channels, the residence time of the reagents in those channels is also relatively small.

The invention can be embodied in other specific forms without departing from the sprit or essential characteristics thereof. The present embodiments therefor are to be considered in all respects as illustrative and not restrictive, the scope of the invention being indicated by the appended claims rather than by the foregoing description, and all changes which come within the meaning and range of equivalency of the claims therefore are intended to be embraced therein.

The invention claimed is:

1. A method of processing a protein sample in a microfluidic device, the method comprising the steps of:
providing a microfluidic device comprising a first fluid network that includes a sample reservoir, a waste reservoir, a plurality of parallel channels connecting the sample reservoir to the waste reservoir, the plurality of parallel channels defining a first region proximate the sample reservoir, a second region adjacent the first region, and a third region proximate the waste reservoir, and a plurality of reagent reservoirs that introduce reagents at various points along each of the plurality of parallel channels, wherein each of the reagent reservoirs is in fluid communication with at least two of the plurality of parallel channels;
maintaining the first region at 50° C. and the third region at a temperature below 50° C. but above room temperature;
placing immobilized trypsin in a portion of each of the plurality of channels in the third region;
placing the protein sample into the sample reservoir;
placing the reagents required to carry out reduction, alkylation, and quenching into the reagent reservoirs;
applying a single negative pressure driving force to the waste reservoir that generates a continuous flow of fluid from the sample reservoir, through the plurality of channels, to the waste reservoir, wherein the flow sequentially exposes the protein sample to the reduction reagent in the first region, and the alkylation and quenching reagents in the second region before the protein sample flows through the immobilized trypsin in the third region; and
collecting the fluid including the protein sample in the waste reservoir.

2. The method of claim 1, wherein the third region is maintained at 37° C.

3. The method of claim 1, wherein the microfluidic device further comprises at least a second fluid network that includes a second sample reservoir, a second waste reservoir, a second plurality of parallel channels connecting the second sample reservoir to the second waste reservoir, and a second plurality of reagent reservoirs that introduce reagents at various points along each of the second plurality of channels.

4. The method of claim 3, wherein the applying a single negative pressure driving force comprises distributing the driving force to each of the waste reservoirs, thereby generating a continuous flow of fluid simultaneously in each of the parallel channels.

5. The method of claim 3, wherein the first fluid network and the second fluid network are identical, each of the first fluid network and the second fluid network including a sample reservoir, a waste reservoir, a plurality of parallel channels connecting the sample reservoir to the waste reservoir, and a plurality of reagent reservoirs that introduce reagents at various points along each of the plurality of parallel channels, and wherein the sample reservoirs of the first fluid network and the second fluid network are arranged with the same center-to-center spacing as the wells in a standard format multiwell plate.

6. The method of claim 5, wherein the placing the protein sample in the sample reservoir comprises placing the protein sample in each of the sample reservoirs using a standard piece of liquid handling equipment.

7. The method of claim 6, wherein the protein samples are placed in the sample reservoirs in an automated process.

8. The method of claim 5, wherein the microfluidic device comprises 24 identical fluid networks.

9. The method of claim 1, wherein the trypsin is immobilized on agarose beads.

10. The method of claim 9, wherein the placing immobilized trypsin in a portion of each of the plurality of channels comprises placing the beads into each of the channel portions such that the beads form a packed bed.

11. The method of claim 1, wherein the placing the protein sample in the sample reservoir comprises transferring the protein sample from a protein manipulation module into the sample reservoir.

12. The method of claim 1, further comprising transferring the protein sample from the waste reservoir to a peptide analysis module.

13. The method of claim 1, wherein each of the plurality of channels has a channel dimension that is ≤1 mm.

14. The method of claim 1, wherein the second region is not maintained at a specific temperature.

15. The method of claim 1, wherein the protein processing is completed in one-fourth the time as compared to protein processing at room temperature.

16. A method of processing a protein sample in a microfluidic device, the method comprising the steps of:
  providing a microfluidic device comprising a fluid network that includes a sample reservoir, a waste reservoir, a plurality of parallel channels connecting the sample reservoir to the waste reservoir, the plurality of parallel channels defining a first region proximate the sample reservoir, a second region adjacent the first region, and a third region proximate the waste reservoir, and a plurality of reagent reservoirs that introduce reagents at various points along each of the plurality of parallel channels, wherein each of the reagent reservoirs is in fluid communication with at least two of the plurality of parallel channels;
  maintaining the third region at 37° C. and the first region at a temperature above 37° C.;
  placing immobilized trypsin in a portion of each of the plurality of channels in the third region;
  placing the protein sample into the sample reservoir;
  placing the reagents required to carry out reduction, alkylation, and quenching into the reagent reservoirs;
  applying a single negative pressure driving force to the waste reservoir that generates a continuous flow of fluid from the sample reservoir, through the plurality of channels, to the waste reservoir, wherein the flow sequentially exposes the protein sample to the reduction reagent in the first region, and the alkylation and quenching reagents in the second region before the protein sample flows through the immobilized trypsin in the third region; and
  collecting the fluid including the protein sample in the waste reservoir.

* * * * *